US009206283B1

(12) United States Patent
Santerre et al.

(10) Patent No.: US 9,206,283 B1
(45) Date of Patent: Dec. 8, 2015

(54) THERMOPLASTIC POLYURETHANE ADMIXTURES

(71) Applicants: Interface Biologics Inc., Toronto (CA); AngioDynamics, Inc., Latham, NY (US)

(72) Inventors: J. Paul Santerre, Whitby (CA); Jeannette Ho, Toronto (CA); Alexandra Piotrowicz, Toronto (CA); Roseita Esfand, Mississauga (CA); Raymond Lareau, Westford, MA (US); Benjamin Bell, Shrewsbury, MA (US)

(73) Assignees: AngioDynamics, Inc., Latham, NY (US); Interface Biologics, Inc., Toronto (CA)

( * ) Notice: Subject to any disclaimer, the term of this patent is extended or adjusted under 35 U.S.C. 154(b) by 0 days.

(21) Appl. No.: 14/210,687

(22) Filed: Mar. 14, 2014

Related U.S. Application Data

(60) Provisional application No. 61/793,691, filed on Mar. 15, 2013.

(51) Int. Cl.
C08G 18/73 (2006.01)
C08G 18/48 (2006.01)
A61L 29/06 (2006.01)
C08G 18/83 (2006.01)

(52) U.S. Cl.
CPC ............. *C08G 18/831* (2013.01); *A61L 29/06* (2013.01); *C08G 18/4825* (2013.01); *C08G 18/73* (2013.01)

(58) Field of Classification Search
None
See application file for complete search history.

(56) References Cited

U.S. PATENT DOCUMENTS

| 3,392,183 | A | 7/1968 | Windemuth et al. |
| 3,427,366 | A | 2/1969 | Verdol et al. |
| 3,872,058 | A | 3/1975 | Gresham |
| 4,312,907 | A | 1/1982 | Hiraoka et al. |
| 4,584,362 | A | 4/1986 | Leckart et al. |
| 4,661,530 | A | 4/1987 | Gogolewski et al. |
| 4,742,090 | A | 5/1988 | Hunter et al. |
| 4,788,083 | A | 11/1988 | Dammann et al. |
| 4,792,354 | A | 12/1988 | Matsuo et al. |
| 4,861,830 | A | 8/1989 | Ward, Jr. |
| 4,994,503 | A | 2/1991 | Harris et al. |
| 5,064,871 | A | 11/1991 | Sciangola |
| 5,145,727 | A | 9/1992 | Potts et al. |
| 5,149,576 | A | 9/1992 | Potts et al. |
| 5,242,995 | A | 9/1993 | Kim et al. |
| 5,395,525 | A | 3/1995 | Takano et al. |
| 5,486,570 | A | 1/1996 | St. Clair |
| 5,542,200 | A | 8/1996 | Matsuoka |
| 5,543,200 | A | 8/1996 | Hargis et al. |
| 5,589,563 | A | 12/1996 | Ward et al. |
| 5,779,897 | A | 7/1998 | Kalthod et al. |
| 5,908,701 | A | 6/1999 | Jennings et al. |
| 5,929,201 | A | 7/1999 | Gibbons et al. |
| 5,954,966 | A | 9/1999 | Matsuura et al. |
| 6,111,049 | A | 8/2000 | Sendijarevic et al. |
| 6,127,485 | A | 10/2000 | Klun et al. |
| 6,127,507 | A | 10/2000 | Santerre |
| 6,254,645 | B1 | 7/2001 | Kellis, Jr. et al. |
| 6,353,057 | B1 | 3/2002 | He et al. |
| 6,448,364 | B1 | 9/2002 | Clatty et al. |
| 8,071,683 | B2 | 12/2011 | Mullick et al. |
| 8,178,620 | B2 | 5/2012 | Mullick et al. |
| 8,187,234 | B2 | 5/2012 | Weaver et al. |
| 8,267,915 | B2 | 9/2012 | Daly et al. |
| 8,317,773 | B2 | 11/2012 | Appling et al. |
| 8,338,537 | B2 | 12/2012 | Mullick et al. |
| 8,377,011 | B2 | 2/2013 | Weaver et al. |
| 8,603,070 | B1 | 12/2013 | Lareau et al. |
| 8,784,402 | B1 | 7/2014 | Lareau et al. |
| 8,876,797 | B2 | 11/2014 | Lareau et al. |
| 2004/0121175 | A1 | 6/2004 | Flexman et al. |
| 2005/0171490 | A1 | 8/2005 | Weaver et al. |
| 2005/0171510 | A1 | 8/2005 | DiCarlo et al. |
| 2005/0176893 | A1 | 8/2005 | Rana et al. |
| 2007/0037891 | A1 | 2/2007 | Esfand et al. |
| 2008/0228253 | A1 | 9/2008 | Mullick et al. |
| 2009/0211968 | A1 | 8/2009 | Ho et al. |
| 2011/0009799 | A1 | 1/2011 | Mullick et al. |
| 2011/0207893 | A1 | 8/2011 | Mullick et al. |
| 2012/0148774 | A1 | 6/2012 | Mullick et al. |
| 2012/0220724 | A1 | 8/2012 | Mullick et al. |
| 2014/0128848 | A1 | 5/2014 | Appling et al. |
| 2014/0276470 | A1 | 9/2014 | Lareau et al. |
| 2015/0038946 | A1 | 2/2015 | Lareau et al. |

OTHER PUBLICATIONS

Carbothane Technical Data Brochure Mar. 2015.*
Ho et al., "The effect of fluorinated surface modifying macromolecules on the surface morphology of polyethersulfone membranes," J Biomater Sci Polym Ed. 11(10):1085-104 (2000).
Ho, "The Effects of Surface Modifying Macromolecules on the Blood Compatibility of Polyethersulfone Membranes Intended for Biomedical Applications," Graduate Department of Chemical Engineering and Applied Chemistry, University of Toronto (167 pages) (1997).
Tang et al., "Surface Modifying Macromolecules for Improved Resistance of Polyurethanes to Biodegradation," Canadian Biomaterials Society Meeting, Quebec City, QC (3 pages) (1994).
Tang et al., "The Use of Surface Modifying Macromolecules to Inhibit Biodegradation of Segmented Polyurethanes," Society for Biomaterials, Boston, MA, (2 pages) (1994).
Tang, "Surface Modifying Macromolecules for Biomaterials," Department of Chemical Engineering, University of Ottawa (172 pages) (1995).

(Continued)

Primary Examiner — Randy Gulakowski
Assistant Examiner — Christopher M Rodd
(74) Attorney, Agent, or Firm — Kristina Bieker-Brady; Clark & Elbing LLP

(57) ABSTRACT

The invention relates to admixtures of thermoplastic polyurethane base polymers that resist surface dulling and fluorinated additives and their use in the manufacture of articles, such as medical devices. For example, the admixtures of the invention are useful in the manufacture of blood dwelling medical devices, such as catheters.

25 Claims, 1 Drawing Sheet

(56) References Cited

OTHER PUBLICATIONS

Tang et al., "Synthesis of surface-modifying macromolecules for use in segmented polyurethanes," Journ App Poly Sci. 62: 1133-45 (1996).

Tang et al., "Use of surface-modifying macromolecules to enhance the biostability of segmented polyurethanes," J Biomed Mater Res. 35(3):371-81 (1997).

Interface Biologics Press Release, "Interface Biologics announces Licensing Partner AngioDynamics has received FDA Clearance for BioFlo PICC with Endexo Technology" <http://www.interfacebiologics.com/news/2012/sep06.htm>, retrieved on Sep. 9, 2013 (2 pages).

Navilyst Medical Press Release, "Navilyst Medical Awarded Contract with HealthPRO Procurement Services, Inc." (2 pages) (2012).

Santerre, "Next-generation Biomaterials Make Catheters Safer", <http://news.engineering.utoronto.ca/next-generation-biomaterials-make-catheters-safer/>, retrieved on Sep. 9, 2014 (3 pages).

* cited by examiner

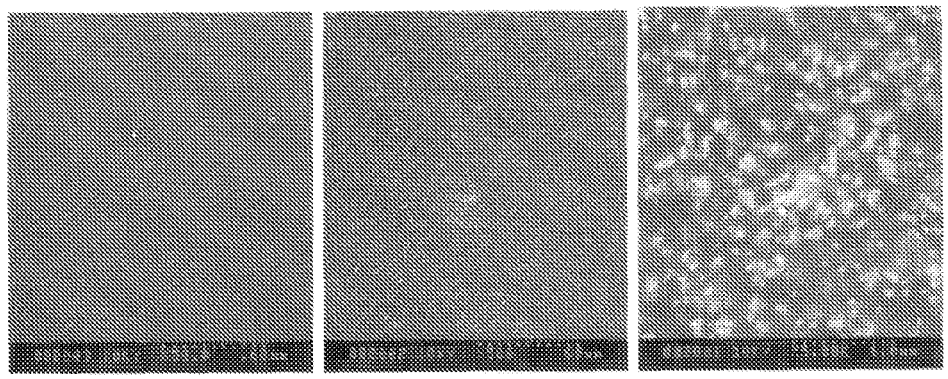
A
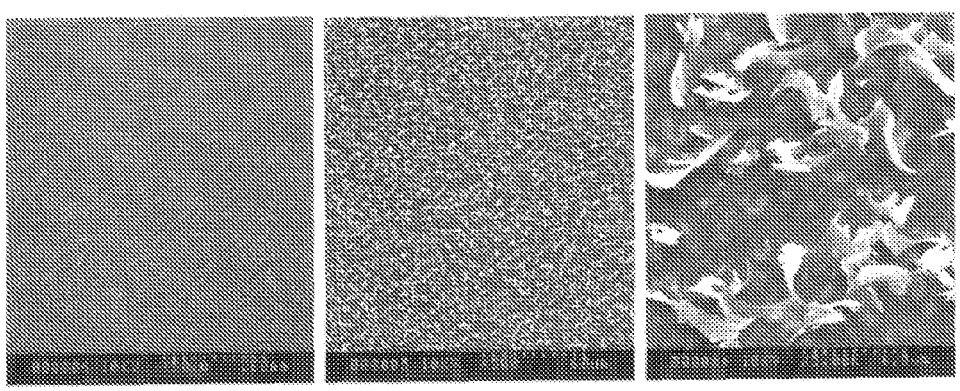
B
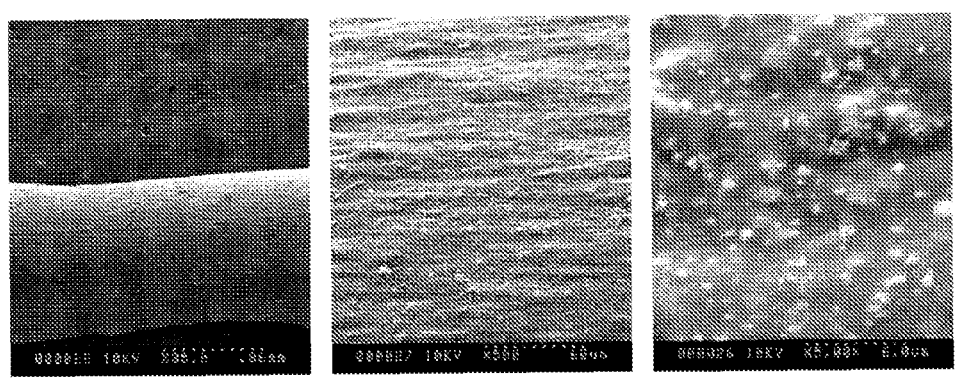
C

THERMOPLASTIC POLYURETHANE ADMIXTURES

CROSS-REFERENCE TO RELATED APPLICATION

This application is a utility application which claims benefit of U.S. Provisional Application No. 61/793,691, filed on Mar. 15, 2013, which is hereby incorporated by reference.

BACKGROUND OF THE INVENTION

The invention relates to admixtures of thermoplastic polyurethane base polymers and fluorinated additives that resist surface dulling and their use in the manufacture of articles, such as implantable medical devices.

Various fluorochemicals have been used to impart water and oil repellency, as well as soil resistance, to a variety of substrates. These fluorochemicals have most often been applied topically (for example, by spraying, padding, or finish bath immersion). The resulting repellent substrates have found use in numerous applications where water and/or oil repellency (as well as soil resistance) characteristics are valued, such as in protective garments for medical technicians and laboratory workers.

Certain low molecular weight fluorinated additives have been used in admixture with base polymers to impart water and oil repellency and/or hemocompatibility. When admixed with a base polymer, the fluorinated additives are sized accordingly to permit migration within, and blooming to the surface of, the base polymer. The advantage of this technical approach is that the surface properties of a polymer can be modified without significantly compromising the properties (e.g., elasticity or tensile strength) of the underlying base polymer. For the fluorinated additives to bloom to the surface of a base polymer, they are manufactured to be relatively small (e.g., typically less than 10,000 Daltons, depending upon the composition of the fluorinated additive and composition of the base polymer).

For particular applications, such as blood dwelling medical devices, it is desirable that the fluorinated additive be modified to avoid compromising the esthetically unpleasing appearance and dulling appearance of the product. We have discovered that this dulling can be controlled by reducing the amount of a specific species called trimer.

SUMMARY OF THE INVENTION

The invention features an admixture including a thermoplastic polyurethane base polymer and a fluorinated additive. These admixtures are useful in the manufacture of implantable devices.

In a first aspect, the invention features an admixture including a thermoplastic polyurethane base polymer having a Shore durometer hardness of between 60A and 85D and a fluorinated additive mixture, wherein the fluorinated additive mixture includes compounds of formula (I):

$$G\text{-}[B\text{-}A]_n\text{-}B\text{-}G \qquad (I),$$

and less than 10% (w/w) trimer of formula (II):

$$G\text{-}B\text{-}G \qquad (II),$$

wherein A is a soft segment including polypropylene oxide, polyethylene oxide, or polytetramethylene oxide, hydrogenated polybutadiene (HLBH), poly (2,2 dimethyl-1-3-propylcarbonate) (PCN), polybutadiene (LBHP), diethyleneglycol-orthophthalicanhydride polyester (PDP), poly(hexamethyhlenecarbonate)diol, hydroxyl terminated polydimethylsiloxanes (PrO-PDMS-PrO) block copolymer, hydrogenated-hydroxyl terminated polyisoprene, poly(ethyleneglycol)-block-poly(propyleneglycol))-block-poly(ethylene glycol), 1,12-dodecanediol, hydrogenated polyisoprene (HHTPI), poly(hexamethylene carbonate), or poly(2-butyl-2-ethyl-1,3-propyl carbonate); B is a hard segment including terminal urethane linkages; G is an polyfluoroalkyl group; and n is an integer from 1 to 15. In particular embodiments, the fluorinated additive mixture includes between 0% and 5% (w/w) (e.g., from 0% to 1.5%, 0% to 2%, 0.1% to 2.2%, 0.3% to 3%, or 0.5% to 5% (w/w)) trimer of formula (II). The polyfluoroalkyl group can be selected from radicals of the general formula $CF_3(CF_2)_rCH_2CH_2$— wherein r is 2-20, and $CF_3(CF_2)_s(CH_2CH_2O)_\chi$ wherein $\chi$ is 1-10 and s is 1-20.

In particular embodiments, the fluorinated additive mixture is formed by a process that includes (i) reacting a hard segment diisocyanate with a soft segment diol to form a prepolymer, and (ii) reacting the prepolymer with a polyfluoroalkyl alcohol to form a mixture of compounds of formula (I).

The soft segment diol can have a theoretical molecular weight of from 400 to 3,000 Daltons (e.g., 400 to 1,200, 800 to 1,600, or 1,200 to 3,000 Da).

The diisocyanate can be selected from 2,4 toluene diisocyanate, 2,6 toluene diisocyanate, methylene bis(p-phenyl)diisocyanate, 1,5 naphtanene diisocyanate, 3,3' bitoluene diisocyanate, methylene bis(p-cyclohexyl isocyanate), 1,6 hexane diisocyanate, 1,12 dodecane diisocyanate, isophorone diisocyanate, cyclohexyl diisocyanate, lysine diisocyanate, and trimethyl-1,6 diisocyanatohexane.

The soft segment diol can be selected from polyalkylene oxide diols, polycarbonate diols, polyester diols, and lactone diols. For example, the soft segment diol can be a polyalkylene oxide diol selected from polyethylene oxide diol, polypropylene oxide diol, and polytetramethylene oxide diol. In particular embodiments, the soft segment diol has a theoretical molecular weight of from 400 to 3,000 Daltons (e.g., 400 to 1,200, 800 to 1,600, or 1,200 to 3,000 Da). In certain embodiments, the diisocyanate is 1,6 hexane diisocyanate. The fluorinated additive mixture can formed by a process that includes (i) reacting about 1 equivalent of the soft segment diol with about 1.4 to 1.8 equivalents (e.g., 1.4 to 1.5, 1.5 to 1.6, 1.6 to 1.7, or 1.7 to 1.8 equivalents) of diisocyanate to form a prepolymer and (ii) reacting the prepolymer with a polyfluoroalkyl alcohol to form the fluorinated additive mixture. In particular embodiments, the fluorinated additive mixture is formed by a process that includes (i) reacting about 1 equivalent of polyalkylene oxide diol with about 1.4 to 1.8 equivalents (e.g., 1.4 to 1.5, 1.5 to 1.6, 1.6 to 1.7, or 1.7 to 1.8 equivalents) of 1,6-hexamethylene diisocyanate to form a prepolymer; and (ii) reacting the prepolymer with a polyfluoroalkyl alcohol to form the fluorinated additive mixture. Optionally, the fluorinated additive mixture is formed by a process that includes an extraction step (e.g., with a hydrocarbon, such as hexane) for removing some or all of the trimer of formula (II). Alternatively, trimer can be removed by dialysis or chromatographic methods. In particular embodiments, the polyfluoroalkyl alcohol is selected from 1H,1H,2H,2H-perfluoro-1-decanol; 1H,1H,2H,2H-perfluoro-1-octanol; 1H,1H,5H-perfluoro-1-pentanol; and 1H,1H, perfluoro-1-butanol, and mixtures thereof.

In any of the above admixtures, the fluorinated additive mixture can have a polystyrene equivalent weight average molar mass, $M_w$, of from 2,000 to 26,000 g/mole (e.g., 6,000±4,000, 8,000±4,000, 10,000±4,000, 12,000±4,000, 18,000±4,000, 20,000±4,000, 22,000±4,000, or 24,000±2,000 g/mole).

In any of the above admixtures, the fluorinated additive mixture can have a polystyrene equivalent number average molar mass, $M_n$, of from 2,000 to 18,000 g/mole (e.g., 6,000±4,000, 8,000±4,000, 10,000±4,000, 13,000±2,000, 14,000±2,000, 15,000±2,000, or 16,000±2,000 g/mole).

In any of the above admixtures, the fluorinated additive mixture can have a polystyrene equivalent molecular weight at highest peak, $M_p$, of from 16,000 to 26,000 g/mole (e.g., 20,000±4,000, 22,000±4,000, or 24,000±2,000 g/mole).

In any of the above admixtures, the fluorinated additive mixture can have a polydispersity index of between 1.0 and 2.0 (e.g., a polydispersity of 1.1 to 1.4, 1.3 to 1.6, 1.35 to 1.55, 1.5 to 1.7, or 1.6 to 1.9).

In any of the above admixtures, the fluorinated additive mixture has a polystyrene equivalent weight average molar mass, $M_w$, of from 2,000 to 14,000 g/mole (e.g., 6,000±4,000, 8,000±4,000, or 12,000±2,000 g/mole), and/or a polystyrene equivalent number average molar mass, $M_n$, of from 2,000 to 12,000 g/mole (e.g., 6,000±4,000, 8,000±4,000, or 10,000±2,000 g/mole), and comprises between 0% and 3% (w/w) (e.g., from 0% to 1.5%, 0% to 2%, 0.1% to 2%, 0.1% to 2.2%, 0.3% to 2.2%, or 0.5% to 2.5% (w/w)) trimer of formula (II).

In any of the above admixtures, the fluorinated additive mixture has a polystyrene equivalent weight average molar mass, $M_w$, of from 14,000 to 26,000 g/mole (e.g., 18,000±4,000, 20,000±4,000, or 22,000±4,000 g/mole), and/or a polystyrene equivalent number average molar mass, $M_n$, of from 10,000 to 16,000 g/mole (e.g., 12,000±2,000 or 14,000±2,000 g/mole), and comprises between 0% and 3% (w/w) (e.g., from 0% to 1.5%, 0% to 2%, 0.1% to 2%, 0.1% to 2.2%, 0.3% to 2.2%, or 0.5% to 2.5% (w/w)) trimer of formula (II).

In certain embodiments, the thermoplastic polyurethane base polymer is a poly(carbonate urethane) base polymer. For example, the thermoplastic polyurethane base polymer can be a poly(carbonate urethane) base polymer including poly(hexamethylene carbonate) and 4,4'-methylene bis(cyclohexyl urethane). In still other embodiments, the poly(carbonate urethane) base polymer has a Shore durometer hardness of between 60A and 85D (e.g., 60A to 95 A, 75A to 90A, 85A to 100A, 5D to 50D, or 25D to 85D).

In particular embodiments, the admixture includes from 1% to 8% (w/w) (e.g., 1% to 6%, 1% to 5%, 2% to 6%, or 3% to 6% (w/w)) fluorinated additive mixture. The admixture can include less than 1%, 0.5%, 0.3%, 0.2%, or 0.1% (w/w) trimer of formula (II) (e.g., from 0 to 1%, 0 to 0.5%, 0 to 0.3%, 0 to 0.2%, or 0.001% to 0.2% (w/w) trimer).

The admixtures of the invention can include other materials, such as radiopaque materials (e.g., as powders or other particulates). Suitable radiopaque additives include bismuth subcarbonate, bismuth oxychloride, bismuth trioxide, tungsten, and preferably barium sulfate (e.g., from 1 to 45% (w/w) radioopaque material). Other additives used in the present invention include colorants such as pigments, dyes, or other suitable colorant materials.

In a related aspect, the invention features a medical device having a surface including an admixture of the invention. The medical device can be a blood dwelling device, such as a catheter (e.g., a central venous catheter, dialysis catheter, implanted port, or peripherally inserted central catheter).

The admixtures of the invention can be used to impart hemo compatibility to a surface. For example, the admixtures can be used to provide a surface for a blood dwelling device having reduced thrombogenicity.

As used herein, the terms "polystyrene equivalent weight average molecular weight" ($M_w$), "polystyrene equivalent number average molecular weight" ($M_n$), and "polystyrene equivalent molecular weight of the highest peak" ($M_p$) refer to polystyrene equivalent values determined by gel permeation chromatography as described in Example 8.

The percentage by weight of trimer in the fluorinated additive mixture is calculated based upon the mass of fluorinated components in the mixture (e.g., excluded from the calculation are the mass of solvents and other non-fluorinated materials that might be included as carriers or other components (e.g., opacifying agents, colorants, anti-oxidants, etc.) that may be also included in the admixture).

Other features and advantages of the invention will be apparent from the Detailed Description, the drawings, and the claims.

DRAWINGS

FIGS. 1A-1C are SEM images of Carbothane™ (Shore Hardness 95 A, with barium sulfate radiopaque filler) films with and without fluorinated additive at magnifications of 50×, 500×, and 5000×. FIG. 1A is Carbothane™ base polymer without fluorinated additive at three magnifications. FIG. 1B is Carbothane™ base polymer compounded with formulation 1 at three magnifications. FIG. 1C is Carbothan base polymer compounded with formulation 7 at three magnifications. At 5000× magnification, a residue is visible for the admixture with formulation 1. In contrast, no residue is observed for the admixture with formulation 7.

DETAILED DESCRIPTION

The methods and compositions of the invention feature admixtures of thermoplastic polyurethane base polymers and fluorinated additive mixtures that resist dulling. The admixtures of the invention are useful in the manufacture of blood dwelling medical devices, such as catheters (i.e., central venous catheter or peripherally inserted central catheter). The medical devices can be fabricated using various processes, including injection molding and extrusion processes resulting from compounded admixture materials.

Applicants have discovered that for admixtures formed from thermoplastic polyurethane base polymers the molecular weight of the fluorinated additive mixture must be (i) low enough to permit migration within, and blooming to the surface of, the base polymer, and (ii) with reduced trimer content to resist dulling Applicants have discovered that trimer content within fluorinated additive mixtures is associated with dulling of the surface leading to esthetically unpleasing product. Admixtures with reduced trimer content can be prepared as described in the examples.

Thermoplastic Polyurethane Base Polymers

Thermoplastic polyurethanes encompass many different types of materials as well as materials of different durometers. Initial selection of a polyurethane may be based on the performance of the material. Thermoplastic polyurethanes are available with Shore Durometers of from 60A to 85D. Thermoplastic polyurethanes come in a variety of different chemical structures, which are selected based upon how the base polymer is being used, and for how long.

Tecoflex medical grade thermoplastic polyurethanes (Grades EG-80A, EG-93A and EG-60D) are a group of aliphatic, polyether based resins that have established credentials for implants including having passed the following standard screening tests: MEM Elution, Hemolysis, USP Class VI, 30 Day Implant, and Ames Mutagenicity.

Tecoflex EG-80A is a medical-grade, aliphatic, polyether-based thermoplastic polyurethane elastomer with a durometer value of 72A. Tecoflex EG-85A is a medical-grade, aliphatic, polyether-based thermoplastic polyurethane elastomer with a durometer value of 77A. Carbothane PC-3575A is a medical-grade, aliphatic, polycarbonate-based thermoplastic polyurethane elastomer with a durometer value of 73A. Carbothane PC-3585A is a medical-grade, aliphatic, polycarbonate-based thermoplastic polyurethane elastomer with a durometer value of 84A.

Bionate thermoplastic polycarbonate polyurethanes are a family of thermoplastic elastomers formed as a reaction product of a hydroxyl terminated polycarbonate, an aromatic diisocyanate and a low molecular weight glycol to form the soft segment.

polymer. A syringe was used to add ca 1.0 mL dibutyltin dilaurate (DBTDL). The reaction mixture was stirred overnight at 45° C. to produce the desired fluorinated polymers.

The polymer was precipitated in deionized water under constant stirring. The volume of water used for the precipitation should be approximately 3.3 times the volume of the DMAc solvent in the solution.

The polymer was purified by dissolution in boiling isopropanol, followed by cooling to 50-60° C., and precipitation by slow addition of hexane. The precipitated polymer was collected on a filter and washed with hexane. The purified polymer was dried in a convection oven at 50° C. for at least 48 hours to produce Formulation 1 (general formula depicted below).

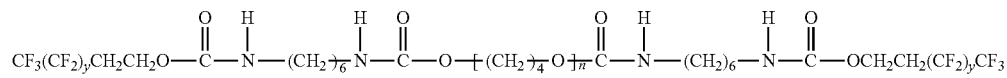

These base polymers can be useful in the admixtures of the invention. It is possible that the elastomeric nature of the base polymers renders them both, ideal for use in catheters, but susceptible to dulling when used in combination with fluorinated additive mixtures having high trimer content.

Exemplary poly(carbonate urethanes) that may be included in the admixtures of the invention include, without limitation, CARBOTHANE®, CHRONOFLEX® AL (aliphatic), CHRONOFLEX® AR (aromatic), CHRONOFLEX® C (aromatic), and BIONATE® (aromatic), in a variety of durometers 80A, 85A, 90A, 95A, 55D, and 75D.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

The fluorinated additives of the invention can be prepared by fractionation, washing, and/or by careful design of the reaction conditions (as described in the examples below). These include, but are not limited to, the component reagents mentioned below.

Reagents
HDI=hexamethylene diisocyanate
PTMO=poly(tetramethylene oxide)diol
FOH C8=(CF$_3$)(CF$_2$)$_5$CH$_2$CH$_2$OH (1H,1H,2H,2H Perfluorooctanol)

EXAMPLE 1

Formulation 1

To dry reactor glassware was added 1 molar ratio of degassed polytetramethylene oxide diol (M$_w$ 1000) and dimethyl acetamide (DMAC). To the solution was added 2 molar ratio of hexamethylene diisocyanate, and the reaction flask was placed in a water bath. 0.5 mL of dibutyltin dilaurate (DBTDL) was added to the system. The reaction mixture was stirred for 4 hours at 65° C. to produce the desired HDI-PTMO prepolymer.

Once the prepolymer reaction is complete, the reactor contents was cooled to 45° C. and degassed FOH C8 was added to the reactor at a molar ratio of 2.3 to end-cap the pre-

EXAMPLE 2

Formulations 2 and 3

Formulation 1 was dissolved in tetrahydrofuran and processed through a GPC prep column. Exiting fractions were collected at 0-31 minutes and 31-43 minutes, corresponding to a high molecular weight fraction (Formulation 2) and low molecular weight fraction (Formulation 3), respectively. A rotary evaporator was used to remove the tetrahydrofuran, and the fractions dried under vacuum overnight. About 550 mg of Formulation 2 and about 250 mg of Formulation 3 were isolated from 1 gram of Formulation 1.

EXAMPLE 4

Formulation 4

Formulation 4 was prepared as described in Example 1, but using a mole ratio of HDI:PTMO of 1.8:1.

EXAMPLE 5

Formulation 5

Formulation 5 was prepared as described in Example 1, but using a mole ratio of HDI:PTMO of 1.67:1.

EXAMPLE 6

Formulation 6

Formulation 6 was prepared as described in Example 1, but using a mole ratio of HDI:PTMO of 1.5:1 (950.5 g PTMO, 239.8 g, HDI, and 398.0 g FOH C8).

EXAMPLE 7

Formulation 7

Formulation 7 was prepared as described in Example 6, but subject to an additional hexane extraction to further reduce the trimer content in the formulation. The solid product of Example 6 was placed in a flask filled with hexane at 50-65° C. with stirring for 2-4 hours. The flask was cooled to 20° C.

and the solid contents allowed to settle. The supernatant was siphoned off, and the solids collected on a filter and dried.

EXAMPLE 8

GPC Analysis of Fluorinated Additives

Gel permeation chromatography (GPC) was used to determine the polymer molecular weight distribution, weight average molecular weight ($M_w$), number average molecular weight ($M_n$), and polydispersity index (PDI). GPC was performed on an Agilent 1100 series instrument (Agilent Technologies Inc, Santa Clara, Calif.) with both an refractive index and UV detector and three phenogel columns ($10^2$ Å, $10^4$ Å and $10^5$ Å pore sizes, Torrence, Calif.) kept at 50° C. Polymer samples were dissolved at 20 mg/ml in THF containing 0.75 ul/ml benzonitrile internal standard, and 30 μL was injected into the system at a flow rate of 1 mL/min. The $M_n$, $M_w$ and PDI were calculated relative to polystyrene standards (Fluka, Buchs, Switzerland) using the GPC software (ChemStation Addon Rev. A.02.02). The results for Formulations 1-7 are provided in Table 1, below.

TABLE 1

| Formulation | HDI:PTMO[1] | $M_w$[2] | $M_n$[2] | Mp[2] | PDI[3] | Trimer (w/w %) |
|---|---|---|---|---|---|---|
| 1 | 2:1 | 11,734 | 8,214 | 11,488 | 1.43 | 15.7% |
| 2 (high MW fraction) | NA | 12,730 | 9,722 | 11,628 | 1.31 | 0% |
| 3 (low MW fraction) | NA | 4,923 | 4,201 | 4,308 | 1.17 | 36.5% |
| 4 | 1.8:1 | 12,703 | 8,748 | 13,150 | 1.45 | 8.8% |
| 5 | 1.67:1 | 16,093 | 11,071 | 17,073 | 1.45 | 6.1% |
| 6 | 1.5:1 | 20,122 | 13,544 | 22,311 | 1.49 | 2.8% |
| 7 | 1.5:1 | 18,822[4] | 12,753[4] | — | 1.47[4] | 0.99%[4] |

1. Mole ratio of hexamethylenediisocyanate to PTMO diol used to form the prepolymer.
2. Polystyrene equivalent (g/mole).
3. Polydispersity Index ($M_w/M_n$).
4. Average of 17 batches.

EXAMPLE 9

Carbothane™ Admixtures

Carbothane™ (Shore Hardness 95 A, with barium sulfate radiopaque filler) was compounded with one or more of formulations 1-7 at 165-210° C. to form an admixture containing 2% (w/w) fluorinated additive. The compounded material was extruded as rods, cut into small pieces, and pressed into films.

The films were placed on plates and incubated at 58-60° C. for 3 days.

Formulations 1 and 3 were observed to form a residue at the surface of the film which leaves a dulling and esthetically unpleasing visual appearance to the product.

In contrast, Formulation 2 formed no residue. With formulations 4 and 5, the amount of the residue was progressively less. In formulations 6 and 7 the residue was not observed.

The results show that the residue at the surface can be reduced or eliminated by reducing the content of trimer in the admixture.

Carbothane™ (Shore Hardness 95A, with barium sulfate radiopaque filler) films without fluorinated additive (FIG. 1A), compounded with formulation 1 (FIG. 1B), and compounded with formulation 7 (FIG. 1C) were analyzed by scanning electron microscopy (SEM) at magnifications of 50×, 500×, and 5000×. At 5000× magnification, a residue is visible, as asperities, for the admixture with formulation 1. In contrast, no residue is observed for the admixture with formulation 7.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. An admixture comprising a thermoplastic polyurethane base polymer having a Shore durometer hardness of between 60A and 85D and a fluorinated additive mixture, wherein said fluorinated additive mixture comprises compounds of formula (I):

$$G\text{-}[B\text{-}A]_n\text{-}B\text{-}G \qquad (I),$$

and between 0.1% and 5% (w/w) trimer of formula (II):

$$G\text{-}B\text{-}G \qquad (II),$$

wherein
A is a soft segment comprising polypropylene oxide, polyethylene oxide, or polytetramethylene oxide, hydrogenated polybutadiene (HLBH), poly(2,2 dimethyl-1-3-propylcarbonate) (PCN), polybutadiene (LBHP), diethyleneglycol-orthophthalicanhydride polyester (PDP), poly(hexamethyhlenecarbonate)diol, hydroxyl terminated polydimethylsiloxanes (PrO-PDMS-PrO) block copolymer, hydrogenated-hydroxyl terminated polyisoprene, poly(ethyleneglycol)-block-poly(propyleneglycol)-block-poly(ethylene glycol), 1,12-dodecanediol, hydrogenated polyisoprene (HHTPI), poly (hexamethylene carbonate), or poly(2-butyl-2-ethyl-1, 3-propyl carbonate);
B is a hard segment comprising terminal urethane linkages;
G is an polyfluoroalkyl group; and
n is an integer from 1 to 15.

2. The admixture of claim 1, wherein said polyfluoroalkyl group is selected from radicals of the general formula $CF_3$  $(CF_2)_r CH_2 CH_2$— wherein r is 2-20, and $CF_3(CF_2)_s$  $(CH_2CH_2O)_\chi$ wherein $\chi$ is 1-10 and s is 1-20.

3. The admixture of claim 1, wherein said fluorinated additive mixture is formed by a process that comprises (i) reacting a diisocyanate corresponding to hard segment B with a diol corresponding to soft segment A to form a prepolymer, and (ii) reacting said prepolymer with a polyfluoroalkyl alcohol corresponding to polyfluoroalkyl group G to form said compounds of formula (I).

4. The admixture of claim 3, wherein said diisocyanate corresponding to hard segment B is selected from 2,4 toluene diisocyanate, 2,6 toluene diisocyanate, methylene bis(p-phenyl)diisocyanate, 1,5 naphthalene diisocyanate, 3,3' bitoluene diisocyanate, methylene bis(p-cyclohexyl isocyanate), 1,6 hexane diisocyanate, 1,12 dodecane diisocyanate, isophorone diisocyanate, cyclohexyl diisocyanate, lysine diisocyanate, and trimethyl-1,6 diisocyanatohexane.

5. The admixture of claim 3 wherein said diol corresponding to soft segment A is selected from polyethylene oxide diol, polypropylene oxide diol, and polytetramethylene oxide diol.

6. The admixture of claim 3, wherein said diol corresponding to soft segment A has a theoretical molecular weight of from 400 to 3,000 Daltons.

7. The admixture of claim 3, wherein said diisocyanate corresponding to hard segment B is 1,6 hexane diisocyanate.

8. The admixture of claim 3, wherein the prepolymer is formed by reacting about 1 equivalent of said diol corresponding to soft segment A with about 1.4 to 1.8 equivalents of said diisocyanate corresponding hard segment B.

9. The admixture of claim 8, wherein said diol corresponding to soft segment A is selected from polyethylene oxide diol, polypropylene oxide diol, and polytetramethylene oxide diol; and wherein the diisocyanate corresponding to hard segment B is 1,6-hexamethylene diisocyanate.

10. The admixture of claim 3, wherein said fluorinated additive mixture is formed by a process that further comprises an extraction step for removing some of said trimer of formula (II).

11. The admixture of claim 3, wherein said polyfluoroalkyl alcohol corresponding to polyfluoroalkyl group G is selected from 1H,1H,2H,2H-perfluoro-1-decanol; 1H,1H,2H,2H-perfluoro-1-octanol; 1H,1H,5H-perfluoro-1-pentanol; and 1H,1H,perfluoro-1-butanol, and mixtures thereof.

12. The admixture of claim 1, wherein said fluorinated additive mixture has a polystyrene equivalent weight average molar mass, $M_w$, of from 2,000 to 26,000 g/mole.

13. The admixture of claim 1, wherein said fluorinated additive mixture has a polystyrene equivalent number average molar mass, $M_n$, of from 2,000 to 18,000 g/mole.

14. The admixture of claim 1, wherein said fluorinated additive mixture has a polystyrene equivalent molecular weight at highest peak, $M_p$, of from 2,000 to 26,000 g/mole.

15. The admixture of claim 9, wherein said fluorinated additive mixture has a polydispersity index of between 1.0 and 2.0.

16. The admixture of claim 1, wherein said fluorinated additive mixture has a weight average molar mass, $M_w$, of from 2,000 to 14,000 g/mole, a number average molar mass, $M_n$, of from 2,000 to 12,000 g/mole, and comprises between 0.3% and 3% (w/w) of said trimer of formula (II).

17. The admixture of claim 1, wherein said fluorinated additive mixture has a weight average molar mass, $M_w$, of from 14,000 to 26,000 g/mole, a number average molar mass, $M_n$, of from 10,000 to 16,000 g/mole, and comprises between 0.3% and 3% (w/w) of said timer of formula (II).

18. The admixture of claim 1, wherein said thermoplastic polyurethane base polymer is a poly(carbonate urethane) base polymer.

19. The admixture of claim 18, wherein said poly(carbonate urethane) base polymer comprises poly(hexamethylene carbonate) and 4,4'-methylene bis(cyclohexyl urethane).

20. The admixture of claim 1, wherein said thermoplastic polyurethane base polymer has a Shore durometer hardness of between 70A and 95A.

21. The admixture of claim 1, wherein said admixture comprises from 1% to 8% (w/w) of said fluorinated additive mixture.

22. The admixture of claim 21, wherein said fluorinated additive mixture comprises 0.1% to 1% (w/w) trimer of formula (II).

23. The admixture of claim 22, wherein said fluorinated additive mixture comprises 0.1% to 0.3% (w/w) trimer of formula (II).

24. A medical device having a surface comprising the admixture of claim 1.

25. The medical device of claim 24, wherein said medical device is a central venous catheter, dialysis catheter, implanted port, or peripherally inserted central catheter.

\* \* \* \* \*